(12) United States Patent
Cosman et al.

(10) Patent No.: US 6,419,680 B1
(45) Date of Patent: *Jul. 16, 2002

(54) CT AND MRI VISIBLE INDEX MARKERS FOR STEREOTACTIC LOCALIZATION

(75) Inventors: Eric R. Cosman, Belmont, MA (US); Theodore S. Roberts, Seattle, WA (US)

(73) Assignee: Sherwood Services AG, Shaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/493,739

(22) Filed: Jun. 22, 1995

Related U.S. Application Data

(63) Continuation of application No. 08/329,659, filed on Oct. 26, 1994, now abandoned, which is a continuation of application No. 08/074,881, filed on Jun. 10, 1993, now abandoned.

(51) Int. Cl.[7] .............................................. A61B 19/00
(52) U.S. Cl. ...................... 606/130; 600/414; 600/426; 378/162
(58) Field of Search ........................... 128/653.1, 653.2, 128/653.4, 653.5, 654; 378/162–164, 204, 205; 606/130; 600/414, 417, 426, 429

(56) References Cited

U.S. PATENT DOCUMENTS

| | | | | |
|---|---|---|---|---|
| 4,826,487 A | * | 5/1989 | Winter | 606/130 X |
| 4,834,713 A | * | 5/1989 | Suthanthiran | 128/899 |
| 4,985,019 A | * | 1/1991 | Michelson | 378/164 X |
| 5,005,578 A | * | 4/1991 | Greer et al. | 600/414 |
| 5,154,179 A | * | 10/1992 | Ratner | 128/653.4 |
| 5,178,146 A | * | 1/1993 | Giese | 128/653.2 |
| 5,186,174 A | * | 2/1993 | Schlundorff et al. | 600/429 |
| 5,222,499 A | * | 6/1993 | Allen et al. | 606/130 X |
| 5,299,253 A | * | 3/1994 | Wessels | 378/163 |
| 5,469,847 A | * | 11/1995 | Zinreich et al. | 128/653.1 |

FOREIGN PATENT DOCUMENTS

| | | | | |
|---|---|---|---|---|
| EP | 0146699 | * | 7/1985 | 128/653.1 |
| RU | 0955916 | * | 9/1982 | 606/130 |

\* cited by examiner

Primary Examiner—Ruth S. Smith

(57) ABSTRACT

This invention relates to skin-based localizer markers that can be placed on the external anatomy of a patient during CT, MRI, or other scanning methods for producing identifiable index marks in stereotactic localization. In a preferred embodiment, the markers are of an annular or axially symmetric geometry, with provision for radiopaque and therefore CT-visible elements and also MRI-visible medium within the marker. The annular shape enables accurate identification of the centroid of the marker in the CT, MRI, or other tomographic image. Because the markers are visible in multi-modal imaging, such as CT and MR, registration of these images or stereotactic indexing can be done from one or both imaging types. In another embodiment, the marker has an index or concave central portion which enables a stereotactic digitized pointer to be placed stably within the indentation during calibration or marker identification in a surgical context. One application of the markers would be for cranial-based, frameless stereotaxy, where a stereotactic digitizing pointer can be used to pick off the positions of the markers in physical space so as to relate the physical space to two-dimensional or three-dimensional imaging data taken from CT or MR scanning.

4 Claims, 3 Drawing Sheets

CT AND MRI VISIBLE INDEX MARKERS FOR STEREOTACTIC LOCALIZATION

This application is a continuation of application Ser. No. 08/329,659, filed on Oct. 26, 1994, now abandoned, which is a continuation of application Ser. No. 08/074,881, filed on Jun. 10, 1993, now abandoned.

BACKGROUND TO THE INVENTION

The field of frame-based and so-called "frameless" stereotaxy is now developing and becoming adopted in the neurosurgical as well as other surgical contexts. In the case of frame-based stereotaxy, a frame is attached to the patient's body, which does or can include a localizer structure such that when tomographic scanning is done with either CT or MRI imaging, fiducial points from the localizer appear on the tomographic slices to index the tomographic images into stereotactic coordinates. In the case of "frameless" stereotaxy, it is desired to not put a frame on the patient prior to tomographic imaging. One of the methods to index the scanner coordinate space to the actual patient physical coordinate space in the operating room is to place index markers either into the patient's bony anatomy, such as the skull, or onto the external anatomy of the patient, such as skin staples or radiopaque marker dots on the patient's skin.

The use of such index markers is illustrated in FIG. 1. Here the patient's head 1 is resting on an external apparatus, in this case a reference plate 6. There are shown several methodologies for frameless stereotactic indexing or localizing. In the first, a mechanical articulated arm consisting of links 3, 4, and 5 with encoded joints between is attached to platform 6. Electronic information from the encoders of the arm is sent via cable 7 to a computer workstation 8. Such an arm can be calibrated to the patient's anatomy 1 by touching off of discrete index points attached to the anatomy, such as markers 2A, 2B, 2C, and 2D. In principle, three non-co-linear index markers could reference the arm by a calibration maneuver to the physical space of the patient's anatomy. This is now being done commonly with mechanical space pointers, and is described in the article by Drs. Guthrie and Adler. The index markers 2A, 2B, 2C, and 2D can be identifiable in tomographic image data taken of the patient's head. That is, the markers may be radiopaque and thus appear in various CT slices. Similarly, the markers could have MRI medium in their composition so that they would be visible on MRI scanning. No such combined index markers have been reported in the literature. Index markers that could be used both for CT and MRI or other imaging would be highly utilitarian, as it would enable registration of multi-modal images and also would enable, with the self-same localizer, physical indexing from a mechanical index arm, such as that shown in FIG. 1.

Many other types of stereotactic localizers are now being reported at conferences and in the literature. For example, also shown in FIG. 1 is an electromagnetic device in which senders or receivers 12A, 12B, and 12C shown in phantom communicate with a sender or receive 11, which is attached to the stereotactic pointer 3. By appropriate triangulation or other spatial indexing, the senders and receivers on the base plate 6 can "know" the position and orientation of the element 11, and thus the space pointer.

Yet another means for frameless localization would be by ultrasonic, sonic, optical, or other transducer means, which could be represented as elements 10A and 10B (shown in phontom) located in the field of the patient, and being received by elements 9A and 9B (shown in phontom) on the probe 3 so as to determine the probe's position and orientation. Several schemes using sonic time of flight sparkers and passive or active optical slices would fall into this category.

The present invention relates to the design and construction of the index markers, such as those illustrated by 2A, 2B, 2C, and 2D in FIG. 1. An objective of the present invention would have these markers be compatible, both to CT, MR, and other localization methods such as P.E.T. scanning or angiography. Yet another objective of the present invention is that these markers would be so constructed that setting the space pointer 3 onto them in a surgical context would enable that the point end of probe 3 could be stably positioned on the marker during the calibration process. For example, if the heads were sterile draped for neurosurgery, one would wish to have the ability through the sterile drape to set the tip of probe 3 onto a marker for a short period of time during marker calibration process. Several embodiments of the present invention described below show how these objectives can be met.

DESCRIPTION OF THE INVENTION

Figure 1:
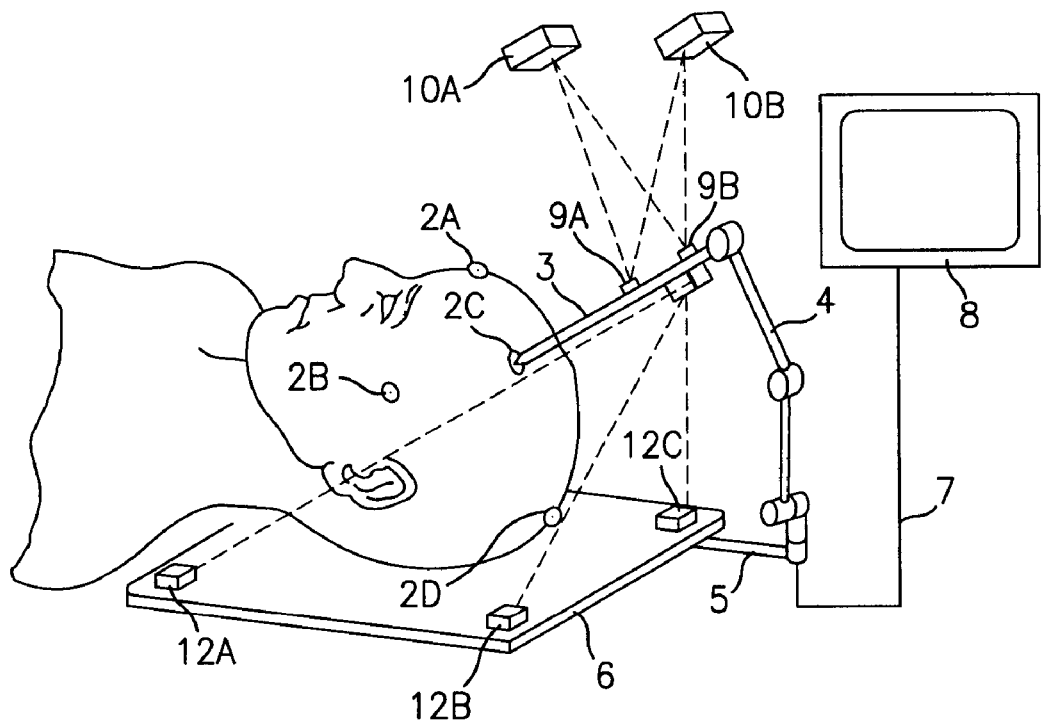
FIG. 1 illustrates the general schematic form for frameless stereotactic calibration using index markers placed on the patient's anatomy.

FIG. 1 has already been described above as background to the invention. It illustrates the methods of stereotactic localization using discrete markers attached to the patient's skull or skin.

Figure 2A:
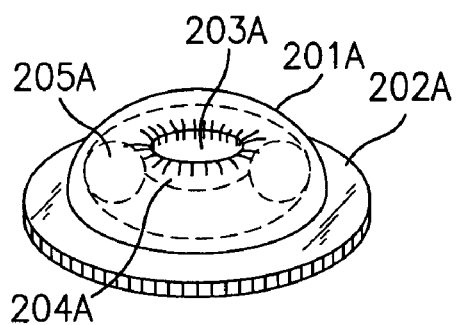
FIGS. 2A, 2B, 2C and 2D shows one embodiment of the present invention with a general annular geometry and indented upper surface for localization, together with the three-dimensional perspective of the scanner images of the marker, as would be seen on, for example, CT and MRI.
Figure 2B:
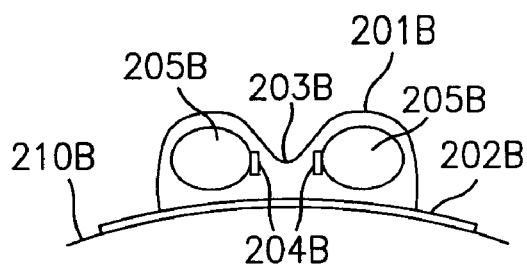
Figure 2C:
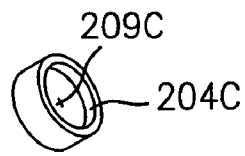
Figure 2D:
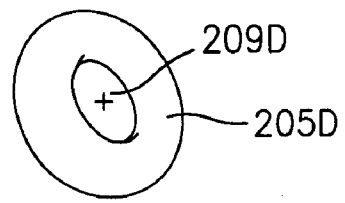

FIG. 2A, 2B, 2C and 2D shows a first embodiment of the present invention which illustrates some of its features. In FIG. 2A, one sees an index marker with a base flange 202A that can be stuck to the patient's skin. FIG. 2B shows an elevation section of this marker stuck to the patient's skin 210B. The flange 202B may have a sticky base, or it may simply be taped down to the skin 210B. There is a dome-shaped structure 201A which has an indented portion 203A on its top surface. On the interior is an annular cavity 205A, which can be filled with fluid or other MRI detectable material. In addition, there is an annular structure 204A which is radiopaque, and thus visible on CT or X-ray film angiography. The FIGS. 2C and 2D show the images 204C of the radiopaque material 204A in FIG. 2A as seen in a three-dimensional reconstruction of a CT image, and also shows the annular image 205D of the MRI visible material in cavity 205A, which would be the three-dimensional reconstruction from an MRI image. In the case of the three-dimensional view of the CT reconstructed image in FIG. 2C, there will be an annular ring 204C, which is seen as an ellipse, depending on the observation direction, and there will be a centroid position 209C, which is the mathematical centroid of this symmetric image structure. That mathematical centroid 209C would then represent a unique point that can be identified from such a symmetrical annular structure that may represent a specific mathematical point within the physical localizer shown in FIG. 2A or 2B. A similar centroid from the MRI image is shown in FIG. 2D and illustrated by number 209D to be at the symmetry center of the MRI reconstructed image 205D. If the annular structures 204B for CT have the same axis and physical center position as the MRI annular structure 205B, as shown in FIG. 2B, then these image-reconstructed centroids 209C and 209D will be coincident with the same physical point relative to the actual index marker. In this way, a unique point from CT and MRI can be determined from the respective image modalities. A similar discussion could be made if the cavity 205A were filled with a fluid visible in P.E.T. (Position Emission Tomography) scanning, or from other future scanning modalities where indices would be required and correlated with CT, MR, P.E.T., etc. It is very convenient to have the same localizer be visible on differing imaging modalities so that correlations of anatomical three-dimensional reconstructions can be made.

Figure 3A:
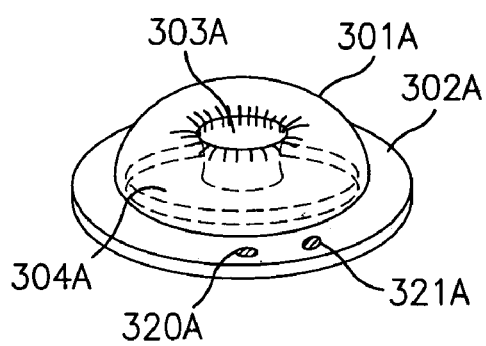
FIGS. 3A and 3B shows another embodiment of the present invention, again with an annular geometry and other means for radiopacity and MRI visibility and with unique marker identification tags.
Figure 3B:
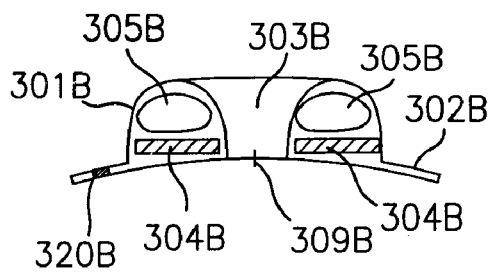

FIGS. 3A and 3B shows another variation of the embodiment of the invention in which again a dome-shaped marker 301A with base 302A and central opening 303A leading to an axial passageway 303B is shown in FIG. 3A. The side elevation view is also shown in FIG. 3B. Again, there is a cavity 305B, which could, for example, contain an MRI-visible fluid, such as copper sulfate or, simply, water. The radiopaque structure 304B is annular and resides just below the MRI annulus 305B. In this case, from a three-dimensional reconstruction, one might attempt to identify a point such as 309B that is along the symmetry axis but below the physical position of the cavity 305B and just on the lower surface and along the central axis of the structure 304B. It would be convenient, if there were several of these fiducial markers placed on the patient's skin at various places, to track their identity by other index structures on the fiducial markers such as those illustrated by dots 320A and 321A. These might be radiopaque dots that could be seen on CT or X-ray film images and distinguish one marker from another by the number and the placement of such dots. In this way, the timing or indexing of the markers relative to the stereotactic frame or imaging device could be easily made from a single view or three-dimensional reconstruction.

Figure 4A:
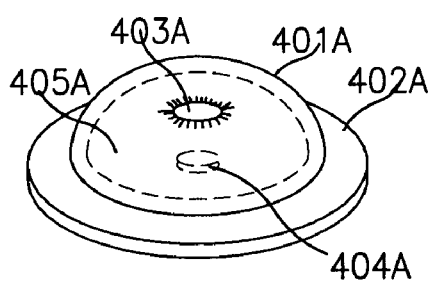
FIGS. 4A and 4B shows yet another embodiment of an annular CT and MRI identifiable index marker.
Figure 4B:
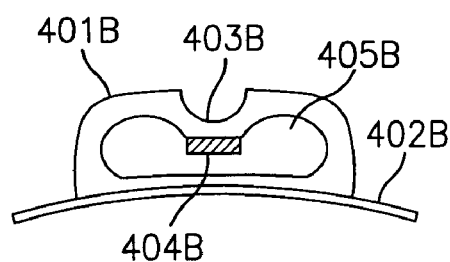

FIGS. 4A and 4B illustrates yet another variation of this dome-shaped marker. In FIG. 4A, the dome 401A contains a cavity 405A and has an indented top surface 403A with radiopaque symmetric structure 404A and base flange 402A. The side elevation again is shown in FIG. 4B. In this situation, the chamber 405B may be generally annular but communicating, and the radiopaque structure 404B has a center of gravity or mathematical centroid which corresponds essentially to the centroid of the chamber 405B. Thus the same type of image reconstructed centroid as discussed with respect to FIG. 2 can be done.

Figure 5:
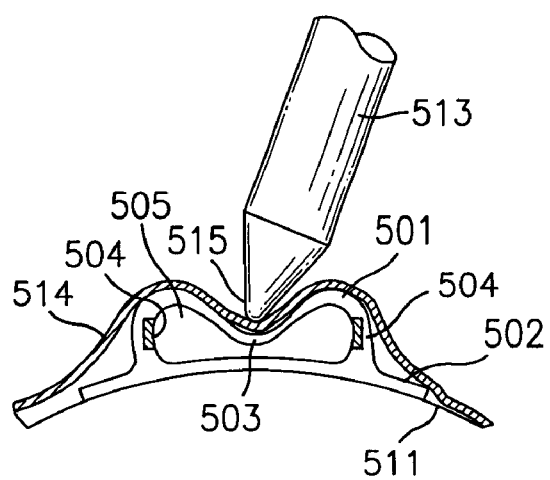
FIG. 5 illustrates how, with an indented upper surface, a marker is amenable to index point identification, even with an overlaid sterile drape.

FIG. 5 shows the convenience and utility of one aspect of the present invention, namely an indented central depression on the top surface of the image marker. The base flange 502 is secured to the skin 511, either by self-sticking adhesive or by the marker being taped in place. There is, as before, an annular dome structure 501 with internal chamber 505 that could be filled with fluid of MRI- or CT-visible material. There is a radiopaque annulus 504 which has a centroid and central axis coinciding with that of the chamber 505. The depressed or indented central portion 503 of the domed chamber 501 represents a stable positioning point for a stereotactic locating probe 513. The tip 515 of the probe 513 can be securely placed at the depression point of the marker 503, and thus a "reading" or calibration event can be taken when the pointer tip 515 is at that position. The tip 515, when in that position, is approximately at the physical centroid of both the annular chamber 505 and the radiopaque annular structure 504, thus making the physical pointer position coincide essentially with an image-reconstructed centroid, as discussed for FIG. 2 above. Furthermore in FIG. 5, a sterile drape 514 is shown, which may cover the scalp 511 and the entire dome structure 501 during surgery. It is convenient to have an entire sterile-barrier over a surgical site, in spite of the fact that such index markers must be accessed. Sterile sheeting, such as 514, comes in a very thin, plastic form, such that when placed over a marker, such as shown in FIG. 5, a pointer, such as 513, may nonetheless be pressed over the centroid of the fiducial marker, thereby depressing the sterile drape 514 into the indentation region 503 to provide a faithful positioning of the tip 515 at the marker centroid. Such ability to place the pointer at the centroid of a marker enhances the accuracy of calibrating the pointer to the marker position, as determined on imaging reconstructions.

Figure 6A:
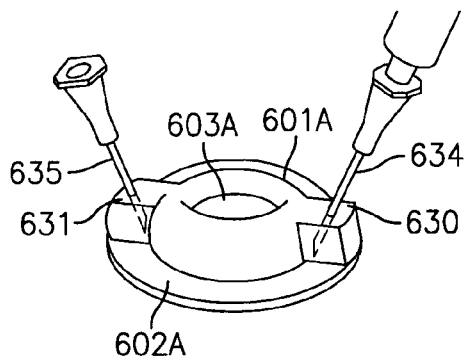
FIGS. 6A and 6B shows a refillable marker that can be injected through re-sealable ports for filling with MRI or P.E.T. visible solutions.
Figure 6B:
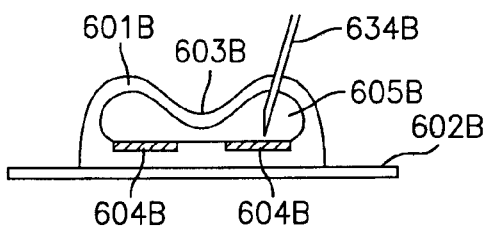

FIGS. 6A and 6B illustrates another aspect of the present invention, namely the ability to fill such a marker repeatedly, or at least for one scanning episode with fluid that will be visible in one or another imaging modality.

FIG. 6A shows an isometric view of the marker, and FIG. 6B shows an elevation section view of the same marker. There are puncturable septums 630 and 631, which enable needles 634 and 635 to be inserted into an inner chamber that communicates with inner chamber 605B. Needle 634 may inject fluid into the fillable chamber 605B, and needle 635 may act as a needle vent so that most of the air can be pushed out. The radiopaque annulus 604B may be a hard backstop so that the needle will not over-penetrate through the base of the marker and hit the scalp or cable below. It is not necessary to have outboard septums as shown in FIG. 6 if the dome 601B itself is puncturable and resealable, as would be the case if it were made out of, for example, silicone rubber. Other ways of venting the air during filling could be conceived, such as depressing the dome with one finger prior to filling or evacuating the dome with a syringe and then allowing the fluid to run in subsequently. Another simple method is to puncture the dome with a needle tip, immerse the marker plus needle under fluid, and pump the chamber with your fingers by squeezing repeatedly. This will fill the chamber. Afterwards, the needle is removed, and the puncture point self-seals.

Figure 7A:
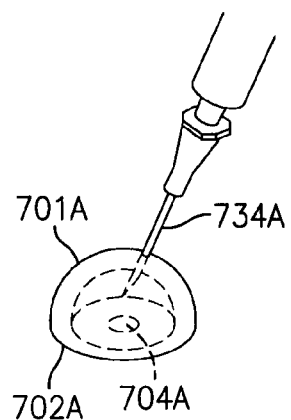
FIGS. 7A, 7B, 7C, 7D, 7E and 7F shows other refillable index markers which have various symmetric and annular geometries that would help in positive identification in CT and MRI three-dimensional image sets.
Figure 7B:
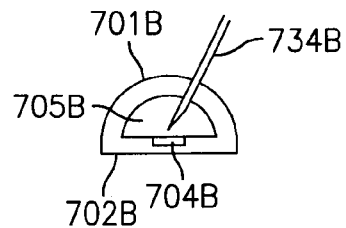
Figure 7C:
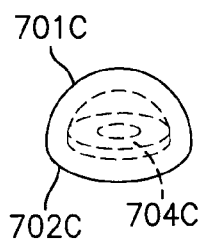
Figure 7D:
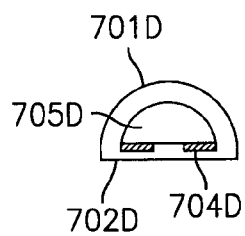
Figure 7E:
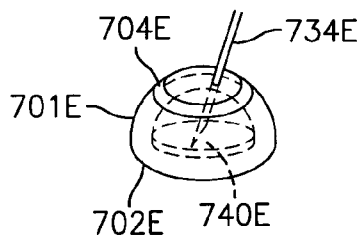
Figure 7F:
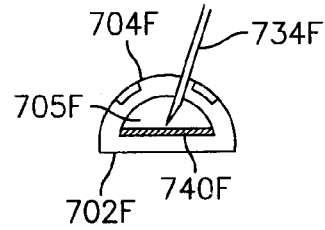

FIGS. 7A, 7B, 7C, 7D, 7E and 7F shows further embodiments of the present invention which illustrates a fillable chamber with radiopaque structures within the chamber or the chamber wall. FIG. 7A is the isometric view of a dome, and FIG. 7B is the section elevation view of the same dome. Element 704A and 704B would be a radiopaque dot at the bottom center of the dome. The dome itself 701A and 701B could be made of a puncturable, resealable rubber material, such as silicone rubber to enable a needle 734A to be inserted into the dome so as to fill the space 705B. When removed, the puncture point will reseal itself. Thus, an MR-visible fluid or a P.E.T.-visible fluid could be used to fill the chamber. FIGS. 7C and 7D show similar respective views for another embodiment of such a chamber which has a radiopaque element 704C and 704D respectively, which is of annular shape so that it will be visible as a ring or ellipse in a 3-D reconstruction from, for example, a CT scan or an angiogram. FIGS. 7E and 7F show similar respective views of another design which has a radiopaque element 704E in the form of a ring that is embedded in the dome surface 701E, which has its symmetry axis on the symmetry axis of the chamber 705F for determining CT and MRI centroid coincidences. Element 740F is a mechanical backstop to prevent over-puncture of needle 734F during filling or fluid withdrawal. In the illustrations of FIGS. 7A–7F, no indentation in the top of the refillable index marker is present. If the marker is sufficiently small, it would be possible to place the tip of the stereotactic localizing probe at the top of the marker and get approximate coincidence of that tip with the centroids of the visible volumes from CT, MRI, Angio, P.E.T., etc.

It is notable that by making symmetric annular or circular visible index volumes, higher precision may be achieved for the mathematical or image centroid of the structure than if one were to use a point-like index structure. This would be the case of differentiating FIG. 7A from FIG. 7C. The point-like CT index structure 704A will be identified in a small voxel region in the CT three-dimensional reconstructed space. The annular structure 704C will be visualized potentially in a larger, three-dimensional voxel space, taking into account many voxels. By taking into account many voxels, both within a CT tomographic slice and among several slices, one can average better the position of the image centroid for such a structure. Thus, using an extended, symmetric structure, advantages can be gained in terms of the accuracy of the mathematical and physical centroid determination of that structure over, for example, a pure point-like object.

It is also notable that there are many other ways to prepare a CT and MRI compatible index marker other than having a needle septum filling means. For example, the marker could be pre-filled and packaged in a packaging medium which had a radiopaque fluid or material in it so that the chamber would not dry out. The chamber could have a screw cap or other hole which would enable filling by simply pumping the chamber digitally or filling it by immersion into a solution. Generally, the invention is meant to include multi-purpose index markers that can be used for CT, MRI, and possibly other imaging modalities. Having described the embodiments shown in the figures, it is noted that those skilled in the art can make variations of the topology shape construction materials, imaging media, and general configuration of the markers that differ from the specific figure example, however, such variations are meant to be included within the scope of the present invention. The variation, for example, may include sets of fiducial markers, each having a different distinguishing feature such as size, color, shape, material, image enhancement, indexing dots, rings, patterns, qualities, etc. This would allow putting many on the patient at different points on the skin to track the stereotactic calibration, mapping, etc. The multiple numbers could be supplied as kits for this purpose, sterile packaged and ready to apply.

We claim:

1. A fiducial marker comprising:
   a base;
   a body structure connected to the base, the body structure configured and dimensional as an annular dome defining a sealed cavity therein;
   an indented central depression being defined by the annular dome, the indented central depression defining an inwardly sloping top surface of the body structure and a central portion, the central portion being a bottom of the indented central depression and intersection of the sloping top surface, the central portion defining a stable positioning point, the stable positioning point being adapted for use with a tip of a stereotactic locating probe;
   a first marker having an annular shape;
   a second marker material disposed within the sealed cavity and being visible to image scanning, wherein the first marker is positioned in juxtaposition with the second marker and
   a first centroid being defined by the first marker and a second centroid being defined by the second marker, wherein the first centroid and the second centroid are configured to be coincident, the stable positioning point being configured to be approximately coincident with the centroid of the first marker and the second marker.

2. The fiducial marker of claim 1, wherein the first marker is a radiopaque structure.

3. The fiducial marker of claim 1, wherein the base includes a flange.

4. The fiducial marker of claim 3, wherein the flange includes a self-sticking adhesive.

\* \* \* \* \*